US011971701B2

(12) United States Patent
Eto

(10) Patent No.: US 11,971,701 B2
(45) Date of Patent: Apr. 30, 2024

(54) INFORMATION PROCESSING APPARATUS, INFORMATION PROCESSING METHOD, AND PROGRAM

(71) Applicant: NEC Corporation, Tokyo (JP)

(72) Inventor: Riki Eto, Tokyo (JP)

(73) Assignee: NEC CORPORATION, Tokyo (JP)

( * ) Notice: Subject to any disclaimer, the term of this patent is extended or adjusted under 35 U.S.C. 154(b) by 410 days.

(21) Appl. No.: 17/442,821

(22) PCT Filed: Mar. 29, 2019

(86) PCT No.: PCT/JP2019/014242
§ 371 (c)(1),
(2) Date: Sep. 24, 2021

(87) PCT Pub. No.: WO2020/202338
PCT Pub. Date: Oct. 8, 2020

(65) Prior Publication Data
US 2022/0221839 A1    Jul. 14, 2022

(51) Int. Cl.
*G05B 19/416*        (2006.01)
*G01N 33/00*         (2006.01)

(52) U.S. Cl.
CPC ....... *G05B 19/416* (2013.01); *G01N 33/0073* (2013.01); *G05B 2219/40573* (2013.01)

(58) Field of Classification Search
CPC ........ G05B 19/416; G05B 2219/40573; G01N 33/0073; G01N 5/02
See application file for complete search history.

(56) References Cited

U.S. PATENT DOCUMENTS

2019/0317066 A1    10/2019   Imamura et al.

FOREIGN PATENT DOCUMENTS

| JP | 2006-120049 A | 5/2006 |
|----|---------------|--------|
| JP | 2010-019107 A | 1/2010 |
| JP | 2017-083188 A | 5/2017 |
| JP | 2017-156254 A | 9/2017 |
| JP | 2018-087722 A | 6/2018 |

OTHER PUBLICATIONS

International Search Report for PCT Application No. PCT/JP2019/014242, dated Jun. 18, 2019.

*Primary Examiner* — Tejal Gami
(74) *Attorney, Agent, or Firm* — Sughrue Mion, PLLC

(57) ABSTRACT

An information processing apparatus (20) includes a model generating unit (210) and a feature value computation unit (220). The model generating unit (210) generates an Auto-Regressive with eXogenous input (ARX) model of a smell sensor by use of input data controlling an input operation of gas including a smell component being a measurement target, and output data acquired by inputting the gas to the smell sensor, based on the input data. The feature value computation unit (220) computes a transfer function of the smell sensor relating to the smell component by subjecting the ARX model to Z-Transform, and further computes a first-order lag transfer function feature value of the smell sensor relating to the smell component by subjecting the transfer function to partial fraction decomposition.

9 Claims, 20 Drawing Sheets

FIG. 2
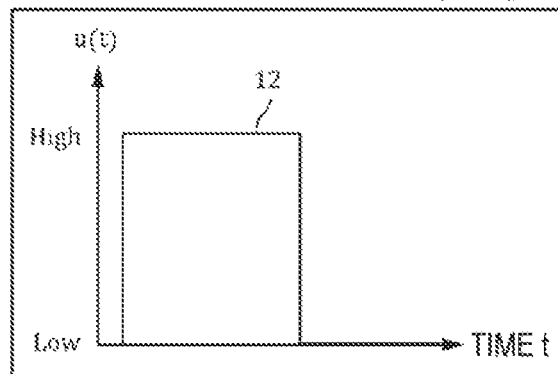
TIME-SERIES DATA OF SIGNAL INPUT VALUE $U = (u(t_1), u(t_2), ..., u(t_f))$
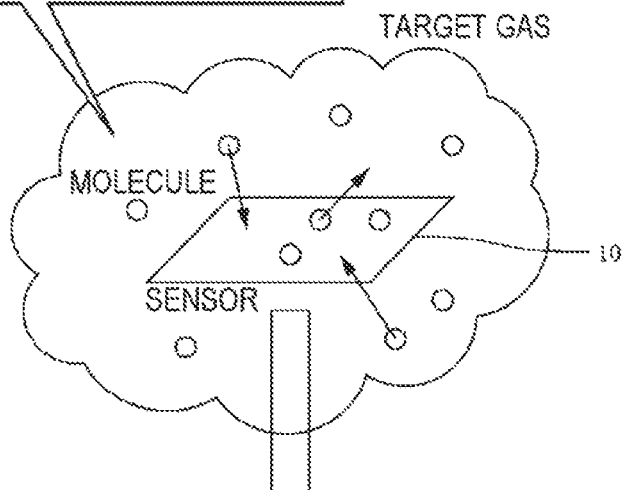
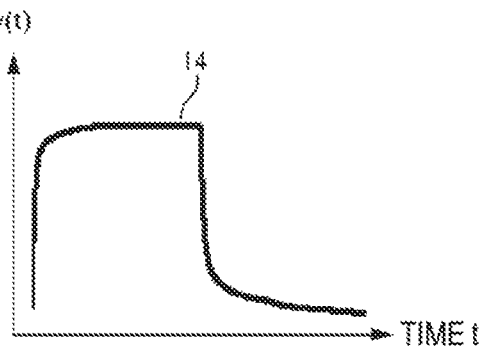
TIME-SERIES DATA OF DETECTION VALUE $Y = (y(t_1), y(t_2), ..., y(t_f))$

FIG. 9

| SMELL COMPONENT | KIND OF SENSORY MEMBRANE | MEASUREMENT ENVIRONMENT (TEMPERATURE) |
|---|---|---|
| i | K, L | T1~T2 |
| i | K, M | T3~T4 |
| i | K, L | T5~T6 |
| j | N, O | T1~T2 |
| ⋮ | ⋮ | ⋮ |

INFORMATION PROCESSING APPARATUS, INFORMATION PROCESSING METHOD, AND PROGRAM

This application is a National Stage Entry of PCT/JP2019/014242 filed on Mar. 29, 2019, the contents of all of which are incorporated herein by reference, in their entirety.

TECHNICAL FIELD

The present invention relates to an analysis technique using a smell sensor.

BACKGROUND ART

A technique for acquiring information relating to gas by measuring the gas with a sensor has been developed. PTL 1 below discloses a technique for determining a kind of sample gas by utilizing a signal (time-series data of a detection value) acquired by measuring the sample gas with a nanomechanical sensor. Specifically, PTL 1 discloses that, since a diffusion time constant of sample gas relative to a receptor of a sensor is determined by a combination of a kind of receptor and a kind of sample gas, the kind of sample gas can be determined based on the diffusion time constant acquired from a signal, and the kind of receptor.

CITATION LIST

Patent Literature

[PTL 1] Japanese Patent Application Publication No. 2017-156254

SUMMARY OF INVENTION

Technical Problem

A technique of PTL 1 performs an analysis of a kind of gas using a feature value acquired from output data of a sensor. However, output data (an output waveform) of a sensor that senses smell is essentially a high-order feature value, and performing an analysis with a high degree of accuracy is difficult. When a dynamic characteristic of a smell sensor can be successfully extracted as a feature value converted to a low order, performing an analysis using a smell sensor with a high degree of accuracy becomes easy.

The present invention has been made in view of the problem described above. One object of the present invention is to provide a technique for improving accuracy of an analysis using a smell sensor.

Solution to Problem

An information processing apparatus according to the present invention includes:
 a model generating unit that generates an Auto-Regressive with eXogenous input (ARX) model of a smell sensor by use of input data controlling an input operation of gas including a smell component being a measurement target, and output data being acquired by inputting the gas to the smell sensor, based on the input data; and
 a feature value computation unit that computes a transfer function of the smell sensor relating to the smell component by subjecting the ARX model to Z-Transform, and further computes a first-order lag transfer function feature value of the smell sensor relating to the smell component by subjecting the transfer function to partial fraction decomposition.

An information processing method performed by a computer according to the present invention includes:
 generating an Auto-Regressive with eXogenous input (ARX) model of a smell sensor by use of input data controlling an input operation of gas including a smell component being a measurement target, and output data being acquired by inputting the gas to the smell sensor, based on the input data; and
 computing a transfer function of the smell sensor relating to the smell component by subjecting the ARX model to Z-Transform, and further computing a first-order lag transfer function feature value of the smell sensor relating to the smell component by subjecting the transfer function to partial fraction decomposition.

A program according to the present invention causes a computer to execute the above-described information processing method.

Advantageous Effects of Invention

According to the present invention, a technique for generating a feature value easy to handle in an analysis using a smell sensor is provided.

BRIEF DESCRIPTION OF DRAWINGS

The above-described object, the other objects, features, and advantages will become more apparent from a suitable example embodiment described below and the following accompanying drawings.

FIG. 2 is a diagram illustrating a sensor for acquiring smell data.

FIG. 9 is a diagram illustrating one example of a database constructed in the third example embodiment.

EXAMPLE EMBODIMENT

Figure 1:
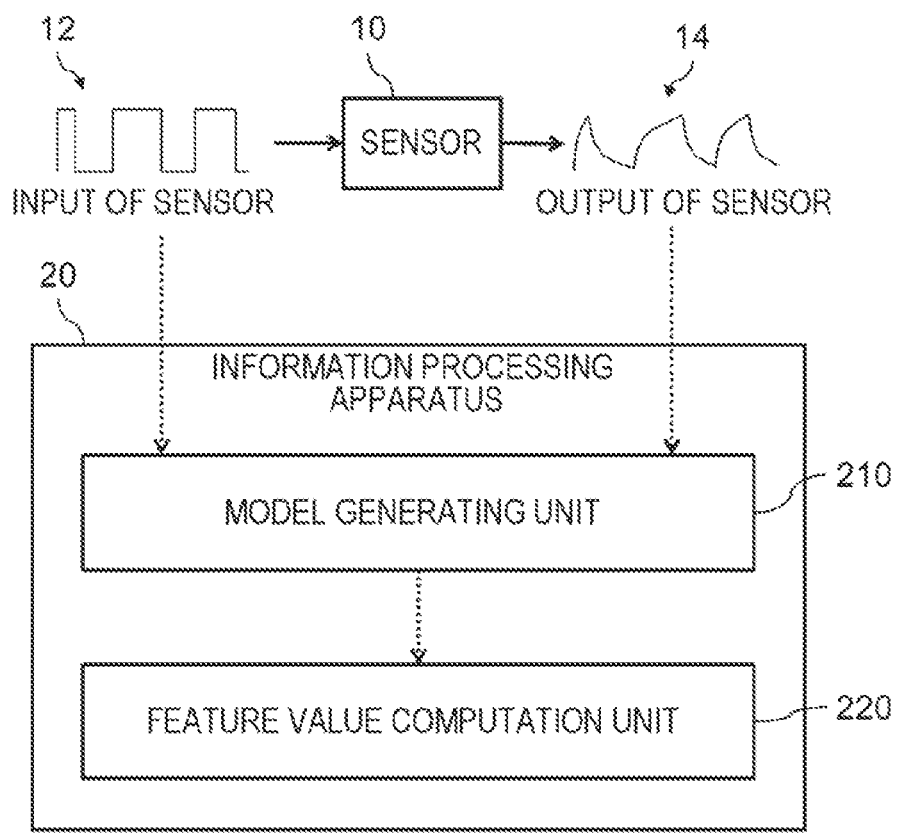
FIG. 1 is a diagram illustrating a functional configuration of an information processing apparatus according to a first example embodiment.

Example embodiments according to the present invention are described below by use of the drawings. Note that, a similar reference sign is assigned to a similar component in all the drawings, and description is not repeated where appropriate. Further, unless otherwise specially described, each block represents, in each block diagram, not a configuration on a hardware basis but a configuration on a function basis. Moreover, a direction of an arrow in the drawings serves for easy understanding of flow of information, and does not limit a direction of communication (one-way communication/two-way communication) unless otherwise specially described.

First Example Embodiment

<Functional Configuration>

FIG. 1 is a diagram illustrating a functional configuration of an information processing apparatus 20 according to a first example embodiment. The information processing apparatus 20 computes information indicating a dynamic characteristic of a sensor 10 by use of an input signal 12 to the sensor 10, and an output signal 14 output from the sensor 10 in association with the input signal 12.

Herein, the sensor 10 is a sensor having a receptor to which a molecule (a smell component) included in gas being a measurement target adheres, as illustrated in FIG. 2, and changing in detection value (output) according to adhesion and separation of a molecule in the receptor. FIG. 2 is a diagram illustrating the sensor 10 for acquiring smell data. The sensor 10 is, for example, a Membrane-type Surface stress Sensor (MSS). The MSS has, as a receptor, a sensory membrane to which a molecule adheres. Then, stress generated in a support member of the sensory membrane changes due to the adhesion and separation of a molecule to and from the sensory membrane. The MSS outputs a detection value based on a change of the stress. Note that, the sensor 10 is not limited to the MSS. The sensor 10 may be a sensor that outputs a detection value, based on a change of a physical amount being related to viscoelasticity or a dynamic characteristic (mass, moment of inertia, or the like) of a member of the sensor 10 resulting according to adhesion and separation of a molecule to and from a receptor. For example, various types of sensors such as cantilever-type, membrane-type, optical, piezoelectric, vibration-response sensors can be applied as the sensor 10.

A detection value (the output signal 14) of the sensor 10 changes due to an operation of exposing gas being a measurement target to the sensor 10 (hereinafter, this is also referred to as a "sampling operation"), and an operation of removing gas being a measurement target from the sensor 10 (hereinafter, this is also referred to as a "purge operation"). For example, a non-illustrated pump mechanism sucks in gas being a measurement target (a sampling operation) in a rising period of the input signal 12 (a period in which a signal level is High). Moreover, the non-illustrated pump mechanism removes gas being a measurement target from the sensor 10 by use of impurity gas (air, or the like) or the like (a purge operation) in a falling period of the input signal 12 (a period in which a signal level is Low). A detection value (the output signal 14) of the sensor 10 varies by control of the sampling operation or the purge operation in response to a value of the input signal 12. In other words, it can be said that an input signal for controlling the sampling operation and the purge operation is equivalent to input to the sensor 10 in a system called the sensor 10. In the following description, as needed, the input signal 12 and the output signal 14 are also referred to as U and Y, respectively. Moreover, a value of the input signal 12 at a time t and a value of the output signal 14 at a time t are also referred to as u(t) and y(t), respectively. U becomes a matrix in which u(t)s are enumerated. Y becomes a matrix in which y(t)s are enumerated.

Returning to FIG. 1, the functional configuration of the information processing apparatus 20 is described. As illustrated, the information processing apparatus 20 according to the present example embodiment includes a model generating unit 210 and a feature value computation unit 220.

The model generating unit 210 learns an input/output relation of the sensor 10 by use of input data of the sensor 10 and output data of the sensor 10, and generates an Auto-Regressive with eXogenous input (ARX) model indicating the input/output relation of the sensor 10. Herein, the input data of the sensor 10 are data that control an input operation (sampling operation/purge operation) of gas including a smell component being a measurement target. As to the example of FIG. 2, the input signal 12 is equivalent to input data. Moreover, the output data of the sensor 10 are data acquired by inputting gas to the sensor 10, based on the input data. As to the example of FIG. 2, the output signal 14 is equivalent to output data.

Herein, an ARX model of the sensor 10 is represented by an equation (1) below. In the equation (1), y(t) is an output of the sensor 10 at a time t, u(t) is an input to the sensor 10 at a time t, $a_i$ (with underline) is an autoregressive coefficient, and $b_i$ (with underline) is an exogenous input coefficient. The model generating unit 210 can learn (generate) an input/output relation of the sensor 10 as an ARX model indicated by the equation (1) below, from, for example, the input signal 12 and the output signal 14 as illustrated in FIG. 2.

[Mathematical 1]

$$y(t) = \sum_{i=1}^{m} \{\underline{a_i} y(t-i) + \underline{b_i} u(t-i)\} \quad (1)$$

Next, the feature value computation unit 220 generates a feature value indicating a characteristic of a sensor by use of the ARX model generated by the model generating unit 210. First, the feature value computation unit 220 performs Z-Transform on the ARX model generated by the model generating unit 210. Further, the feature value computation unit 220 computes a transfer function of a first-order lag system by subjecting, to partial fraction decomposition, a result of subjecting the ARX model to Z-Transform.

The feature value computation unit 220 first acquires an equation (2) below by subjecting, to Z-Transform, the ARX model indicated by the equation (1). In the equation (2) below, Y(z)/U(z) is a ratio of Z-Transform of an output Y to an input U of a sensor (i.e., a transfer function in a Z-area).

[Mathematical 2]

$$\frac{Y(z)}{U(z)} = \frac{\sum_{i=1}^{m} b_i z^{-i}}{1 - \sum_{i=1}^{m} a_i z^{-i}} \quad (2)$$

Further, the feature value computation unit 220 acquires a following equation by subjecting a right side of the equation (2) to partial fraction decomposition.

[Mathematical 3]

$$\frac{Y(z)}{U(z)} = \sum_{i=1}^{m} \frac{\tilde{b}_i}{z - a_i} \quad (3)$$

In the equation (3), $a_i$ indicates a feature value relating to a desorption rate of a smell component i, and $\tilde{b}_i$ (with tilde) indicates a feature value relating to an adsorption rate of the smell component i. Note that, $\tilde{b}_i$ with tilde is also referred to briefly as "$b_i$" in the following description. The feature value computation unit 220 acquires a pair of $a_i$ and $\tilde{b}_i$ as a first-order lag transfer function feature value, as indicated in an equation (4) below.

$$\{a_i, \tilde{b}_i\}_{i=1}^{m} \quad \text{[Mathematical 4]}$$

WHERE $a_i := (1 - \Delta t \beta_i)$, $\tilde{b}_i := \Delta t \gamma_i \alpha_i \rho_i$, Note that, in the equation (4) above, $\alpha_i$ indicates an adsorption rate of the smell component i, $\beta_i$ indicates a desorption rate of the smell component i, $\gamma_i$ indicates a proportionality constant of the number of molecules adhering to a sensor receptor relating to the smell component i and a sensor output generated thereby, $\rho_i$ indicates density of the smell component i, and $\Delta t$ indicates a time interval in a discrete-time system. The first-order lag transfer function feature value represented by the equation (4) above can be utilized as a feature value representing a combination of a sensory membrane being set in the sensor 10 and the smell component i. Moreover, dynamics of the sensor 10 is physically interpretable for each smell component i from the above-described relational expression of $a_i$ and $\tilde{b}_i$.

A first-order lag transfer function feature value acquired by the present example embodiment is a feature value of an order lower than output data of the sensor 10. Accuracy of a discrimination analysis or a regression analysis can be improved by using the first-order lag transfer function feature value converted to a low order in this way.

<Hardware Configuration of Information Processing Apparatus 20>

Each functional configuration unit of the information processing apparatus 20 may be achieved by hardware (example: a hard-wired electronic circuit, or the like) that achieves each functional configuration unit, or may be achieved by a combination of hardware and software (example: a combination of an electronic circuit and a program controlling the electronic circuit, or the like). A case where each functional configuration unit of the information processing apparatus 20 is achieved by a combination of hardware and software is further described below.

Figure 3:
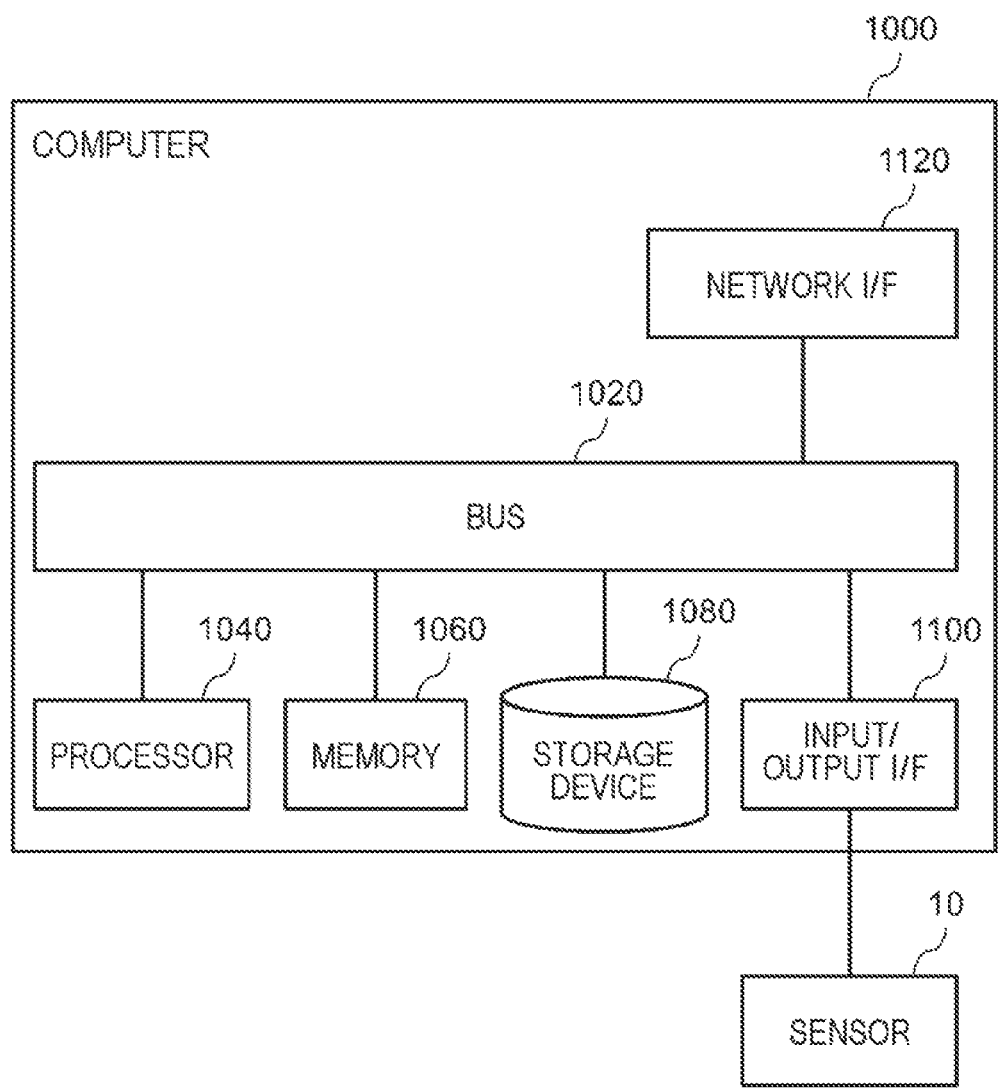
FIG. 3 is a diagram illustrating a computer for achieving the information processing apparatus.

FIG. 3 is a diagram illustrating a computer 1000 for achieving the information processing apparatus 20. The computer 1000 is any computer. For example, the computer 1000 is a stationary computer such as a personal computer (PC) or a server machine. Alternatively, for example, the computer 1000 is a portable computer such as a smartphone or a tablet terminal. The computer 1000 may be a dedicated computer designed to achieve the information processing apparatus 20, or may be a general-purpose computer.

The computer 1000 includes a bus 1020, a processor 1040, a memory 1060, a storage device 1080, an input/output interface 1100, and a network interface 1120. The bus 1020 is a data transmission path through which the processor 1040, the memory 1060, the storage device 1080, the input/output interface 1100, and the network interface 1120 transmit/receive data to/from each other. However, a method of mutually connecting the processor 1040 and the like is not limited to bus connection.

The processor 1040 includes various types of processors such as a central processing unit (CPU), a graphics processing unit (GPU), and a field-programmable gate array (FPGA). The memory 1060 is a main storage apparatus achieved by use of a random access memory (RAM) or the like. The storage device 1080 is an auxiliary storage apparatus achieved by use of a hard disk, a solid state drive (SSD), a memory card, a read only memory (ROM), or the like.

The input/output interface 1100 is an interface for connecting the computer 1000 and an input/output device. For example, an input apparatus such as a keyboard or a touch panel, and an output apparatus such as a display device or a speaker are connected to the input/output interface 1100.

The network interface 1120 is an interface for connecting the computer 1000 to a communication network. The communication network is, for example, a local area network (LAN) or a wide area network (WAN). A method of connecting the network interface 1120 to the communication network may be wireless connection or may be wired connection.

The storage device 1080 stores a program module that achieves each functional configuration unit (the model generating unit 210, the feature value computation unit 220, and the like) of the information processing apparatus 20. The processor 1040 reads each of the program modules onto the memory 1060, executes the read program module, and thereby achieves a function being associated with each of the program modules.

<Flow of Processing>

Figure 4:
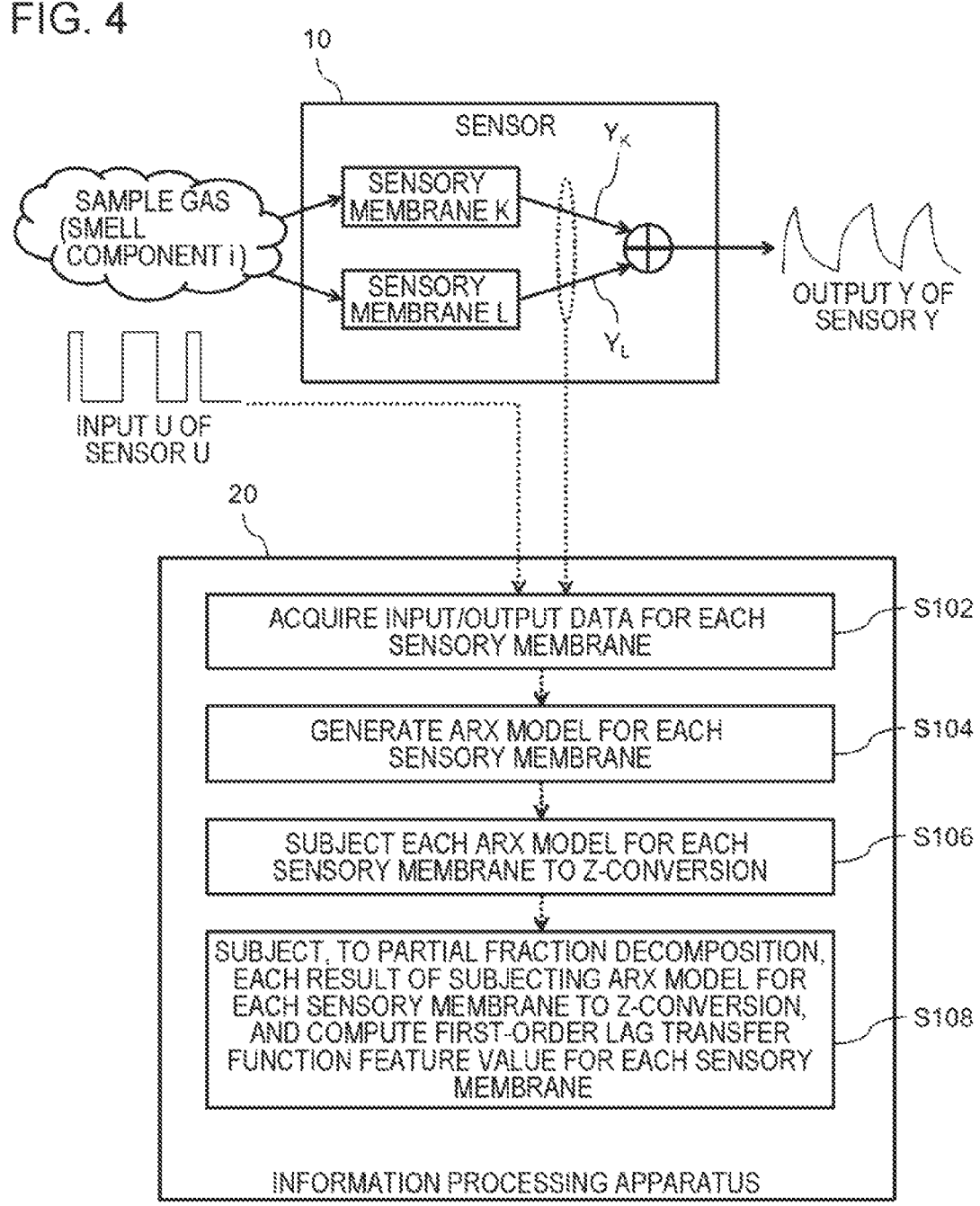
FIG. 4 is a diagram illustrating a flow of processing executed by the information processing apparatus according to the first example embodiment.

FIG. 4 is a diagram illustrating a flow of processing executed by the information processing apparatus 20 according to the first example embodiment. In the example of FIG. 4, the sensor 10 has two sensory membranes (a sensory membrane K and a sensory membrane L). Moreover, in the example of FIG. 4, sample gas having the smell component i is input to the sensor 10 in response to an input signal U (e.g., an M-sequence signal) having a random sampling period. The output Y of the sensor 10 in this case is a sum of an output of the sensory membrane K and an output of the sensory membrane L.

First, the model generating unit 210 acquires input/output data for each sensory membrane (S102). For example, the model generating unit 210 acquires input data U to the sensor 10 and output data $Y_K$ of the sensory membrane K as input/output data of the sensory membrane K. Moreover, the model generating unit 210 acquires input data U to the sensor 10 and output data $Y_L$ of the sensory membrane L as input/output data of the sensory membrane L. Then, the model generating unit 210 generates an ARX model for each sensory membrane, based on input/output data for each sensory membrane (S104). For example, the model generating unit 210 generates an ARX model regarding the sensory membrane K, based on the input data U to the sensor 10 and the output data $Y_K$ of the sensory membrane K. Moreover, the model generating unit 210 generates an ARX model regarding the sensory membrane L, based on the input data U to the sensor 10 and the output data $Y_L$ of the sensory membrane L. Then, the feature value computation unit 220 performs Z-Transform on the ARX model generated for each sensory membrane (S106). Then, the feature value computation unit 220 subjects, to partial fraction decomposition, each result of subjecting each ARX model to Z-Transform, and computes a first-order lag transfer function feature value for each sensory membrane (S108).

Modification Example

A model generating unit 210 may be configured in such a way as to extract a plurality of pieces of partial input data and a plurality of pieces of partial output data by use of a plurality of windows, and generate a plurality of ARX models.

Figure 5:
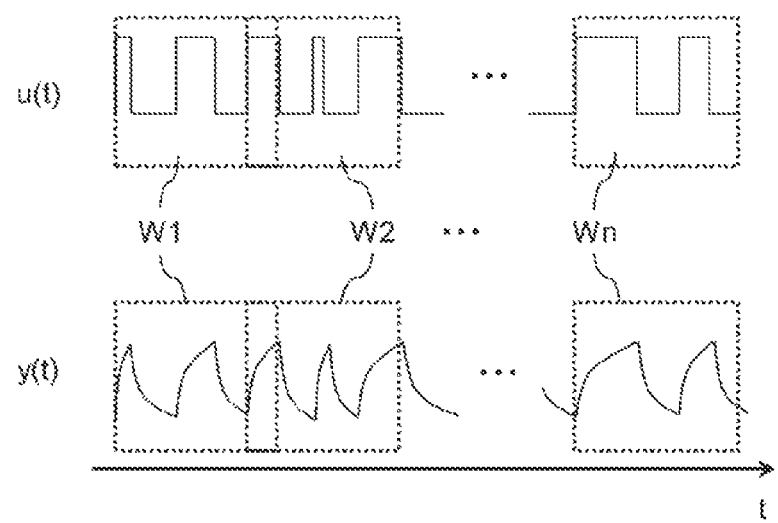
FIG. 5 is a diagram illustrating an example of extracting a plurality of pieces of partial input data and a plurality of pieces of partial output data by use of a plurality of windows.

FIG. 5 is a diagram illustrating an example of extracting a plurality of pieces of partial input data and a plurality of pieces of partial output data by use of a plurality of windows. In the example illustrated in FIG. 5, n pairs of partial input data and partial output data are extracted from input data u(t) and output data y(t) by use of a plurality of windows W1 to Wn. A width of one window is set as a such a width that a frequency component equal to or more than a predetermined reference is included in the input data u(t). For example, the model generating unit 210 can determine a continuous time area covering a frequency component equal to or more than the reference by subjecting the input data u(t) to Fourier transform, and determine a width of the area as a width of one window. Note that, as illustrated in FIG. 5, the model generating unit 210 may determine a position of each window in such a way that two adjacent windows (example: W1 and W2) partially overlap each other.

The model generating unit 210 generates an ARX model by use of one pair of partial input data and partial output data extracted for each window as the above-described input data and output data. In other words, the model generating unit 210 generates a plurality of ARX models by use of a plurality of pieces of partial input data and a plurality of pieces of partial output data extracted by use of a plurality of windows.

Then, a feature value computation unit 220 computes a plurality of first-order lag transfer function feature values by subjecting the plurality of ARX models to Z-Transform and partial fraction decomposition. Then, the feature value computation unit 220 executes machine learning by use of the plurality of computed first-order lag transfer function feature values as learning data, and determines a first-order lag transfer function feature value of the sensor 10. Moreover, the feature value computation unit 220 may be configured in such a way as to determine a first-order lag transfer function feature value of the sensor 10 after performing statistical processing such as abnormal value removal on the plurality of computed first-order lag transfer function feature values.

The configuration according to the present modification example allows acquisition of a first-order lag transfer function feature value having a higher degree of accuracy as compared with a case of computing a first-order lag transfer function feature value (a feature value indicating a dynamic characteristic of the sensor 10) by use of one ARX model.

Second Example Embodiment

In the present example embodiment, one example of application of a first-order lag transfer function feature value is described. When two or more sensory membranes differing in kind from each other are set in a sensor 10, an information processing apparatus 20 can generate a feature value being robust against a change of a measurement environment by use of a first-order lag transfer function feature value for each sensory membrane.

Figure 6:
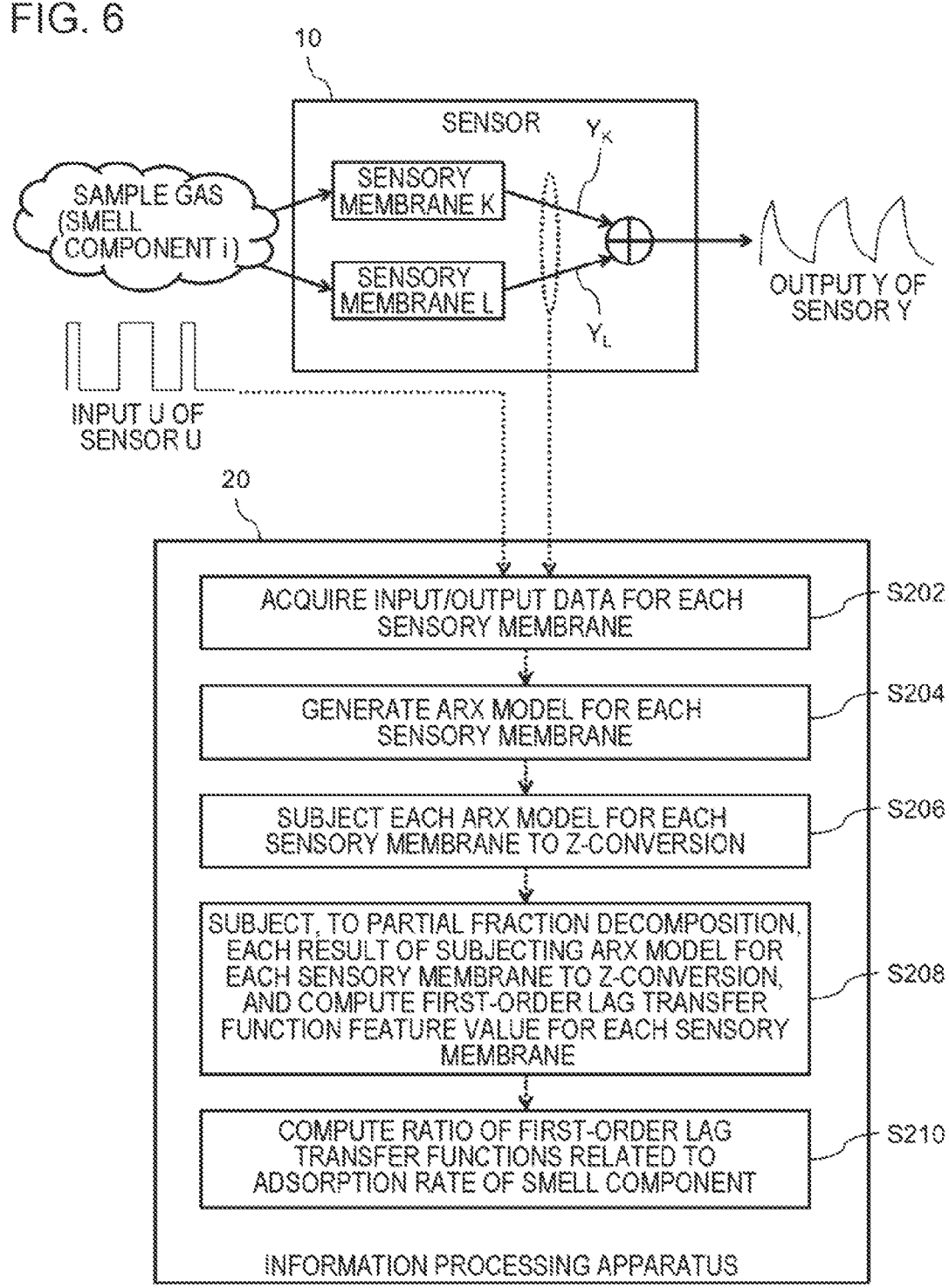
FIG. 6 is a diagram illustrating a flow of processing executed by an information processing apparatus according to a second example embodiment.

FIG. 6 is a diagram illustrating a flow of processing executed by the information processing apparatus 20 according to a second example embodiment. In the example of FIG. 6, the sensor 10 has two sensory membranes (a sensory membrane K and a sensory membrane L) differing in kind from each other. Moreover, in the example of FIG. 6, sample gas having a smell component i is input to the sensor 10 in response to an input signal U (e.g., an M-sequence signal) having a random sampling period. An output Y of the sensor 10 in this case is a sum of an output of the sensory membrane K and an output of the sensory membrane L.

First, a model generating unit 210 acquires input/output data for each sensory membrane, in response to measurement of the sample gas including a smell component i (S202). Then, the model generating unit 210 generates an ARX model for each sensory membrane, based on input/output data for each sensory membrane (S204). Then, the feature value computation unit 220 subjects the ARX model for each sensory membrane to Z-Transform (S206). Further, the feature value computation unit 220 computes a first-order lag transfer function feature value $(a_i, b_i)$ for each sensory membrane by subjecting, to partial fraction decomposition, a result of subjecting the ARX model to Z-Transform (S208). The processing in S202 to S208 is similar to the processing in S102 to S108 in FIG. 4. Then, the feature value computation unit 220 computes a ratio of the first-order lag transfer function feature values $b_i$s related to an adsorption rate of the smell component i, with regard to the sensory membrane K and the sensory membrane L (S210). Note that, in the following description, a ratio between a first-order lag transfer function feature value $b_{iK}$ and a first-order lag transfer function feature value $b_{iL}$ is also referred to as "$b_{iK}/b_{iL}$".

Herein, an output of the sensor 10 can vary in response to not only a kind of smell component being a measurement target, but also an environment (e.g., temperature, humidity, or the like at measurement) in which the smell component is measured. Note that, an output of the sensor 10 varies depending on a change of stress generated in a support member by a smell component adhering to a sensory membrane set in the sensor 10, as described by use of FIG. 2. In other words, when "an output of the sensor 10 changes due to a measurement environment", it can be considered that "an adsorption rate of a sensory membrane set in the sensor 10 varies in response to a change of the measurement environment". Further, it is assumed that an adsorption rate of a sensory membrane can be expressed by a product of a parameter varying depending on a measurement environment and a parameter specific for each kind of sensory membrane. Based on this assumption, a parameter part depending on a change of a measurement environment is cancelled by performing processing (processing of computing a ratio of first-order lag transfer function feature values related to an adsorption rate of a smell component) in S202. In other words, a ratio ($b_{iK}/b_{iL}$) between a first-order lag transfer function feature value acquired with regard to the sensory membrane K and a first-order lag transfer function feature value acquired with regard to the sensory membrane L can be utilized for an analysis of the smell component i as a feature value being robust against a change of a measurement environment.

Note that, the above-described assumption has an ideal that a parameter specific for each kind of sensory membrane is always a constant value regardless of a measurement environment. However, in reality, it can hardly be said that a parameter specific for each membrane kind is not at all affected by a change of a measurement environment. Thus, the information processing apparatus 20 may be configured in such a way as to perform the following processing.

First, the sensor 10 measures sample gas including the smell component i under environments differing from each other a plurality of times. For each single measurement, the model generating unit 210 generates each of an ARX model regarding the sensory membrane K and an ARX model regarding the sensory membrane L, and the feature value computation unit 220 computes, based on the ARX models of the sensory membranes K and L, the first-order lag transfer function feature values "$b_{iK}$" and "$b_{iL}$" related to an adsorption rate of the smell component i, respectively. Moreover, the feature value computation unit 220 acquires the ratio "$b_{iK}/b_{iL}$" of the first-order lag transfer function feature values "$b_{iK}$" and "$b_{iL}$" for each single measurement. Then, the feature value computation unit 220 determines, based on a plurality of "$b_{iK}/b_{iL}$" acquired by a plurality of times of measurements, a range of a measurement environment in which "$b_{iK}/b_{iL}$" becomes constant (an inclination is 0). Then, the feature value computation unit 220 stores, in a storage area such as a storage device 1080, information indicating the determined range of the measurement environment, in association with information indicating a kind of smell component and information indicating a kind of sensory membrane (a combination of sensory membranes).

Figure 7:
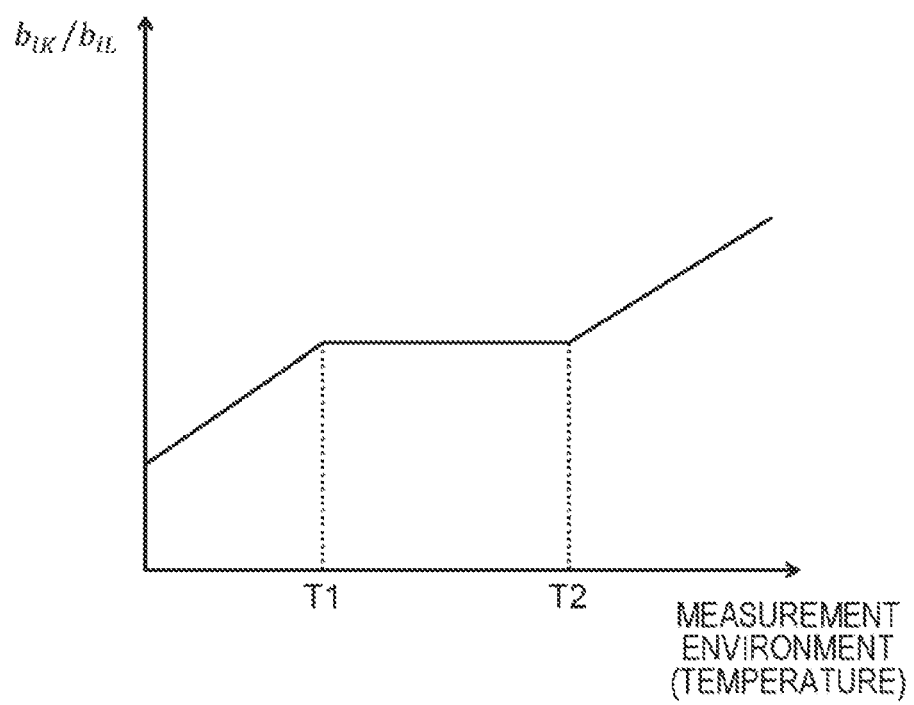
FIG. 7 is a diagram illustrating a result of "biK/biL" acquired by measuring sample gas including a smell component under differing environments a plurality of times.

For example, it is assumed that a result as illustrated in FIG. 7 is acquired with regard to "$b_{iK}/b_{iL}$" when the sensor 10 having the sensory membrane K and the sensory membrane L measures sample gas including the smell component i under differing environments a plurality of times. FIG. 7 is a diagram illustrating a result of "$b_{iK}/b_{iL}$" acquired by measuring sample gas including the smell component i under differing environments a plurality of times. In FIG. 7, a horizontal axis indicates a "measurement environment (temperature)", and a vertical axis indicates the "ratio ($b_{iK}/b_{iL}$) of the first-order lag transfer function feature value $b_{iK}$ when the first-order lag transfer function feature value $b_{iL}$ is determined as a reference.

In the example of FIG. 7, "$b_{iK}/b_{iL}$" is constant in a temperature range of T1 to T2, and varies in value in response to a change of a measurement environment in other ranges. In this case, the feature value computation unit 220 determines a temperature range of T1 to T2 in which a value of "$b_{iK}/b_{iL}$" is constant (i.e., an inclination is 0). Note that, the feature value computation unit 220 may be configured in such a way as to determine a range in which an inclination satisfies a predetermined reference (e.g., −0.05 or more and 0.05 or less). Then, the feature value computation unit 220 stores, in a storage area such as the storage device 1080, information indicating a temperature range of T1 to T2, in association with information indicating the smell component i and information indicating a combination of the sensory membrane K and the sensory membrane L. Herein, information stored in the storage device 1080 is information indicating a condition in which a feature value being robust against a change of a measurement environment can be acquired.

The configuration according to the present example embodiment allows generation of a database that accumulates a condition (a combination of a kind of smell component, a kind of sensory membrane, and a measurement environment) in which a feature value being robust against a change of a measurement environment can be acquired. The database can be utilized, for example, as described in a third example embodiment.

Third Example Embodiment

<Functional Configuration>

Figure 8:
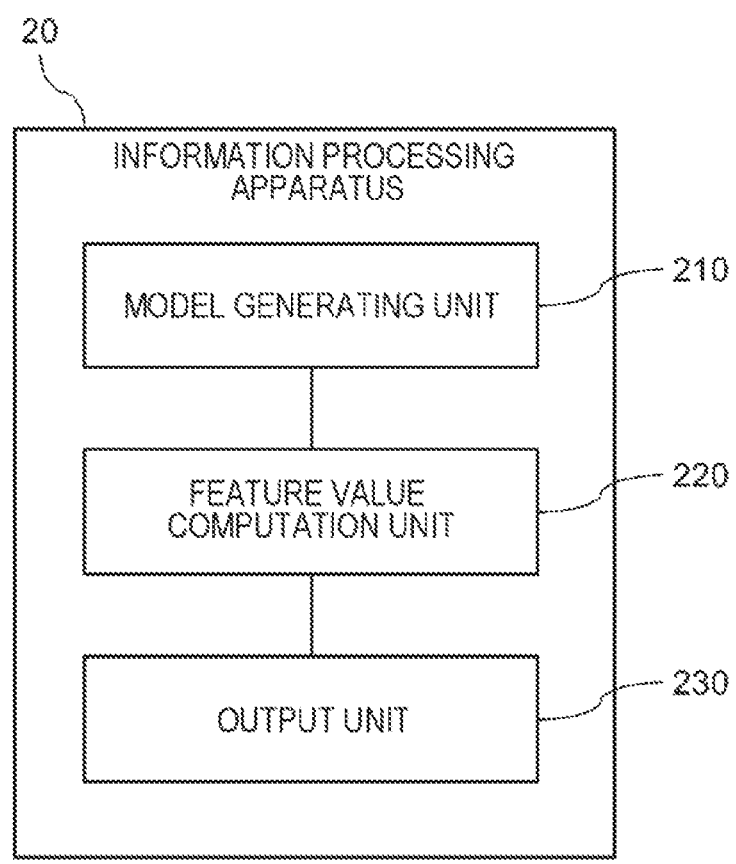
FIG. 8 is a diagram illustrating a functional configuration of an information processing apparatus according to a third example embodiment.

FIG. 8 is a diagram illustrating a functional configuration of an information processing apparatus 20 according to a third example embodiment. The information processing apparatus 20 according to the present example embodiment is configured in such a way as to further include a processing unit (an output unit 230) that utilizes information accumulated in a storage area such as a storage device 1080 in the second example embodiment.

Figure 10:
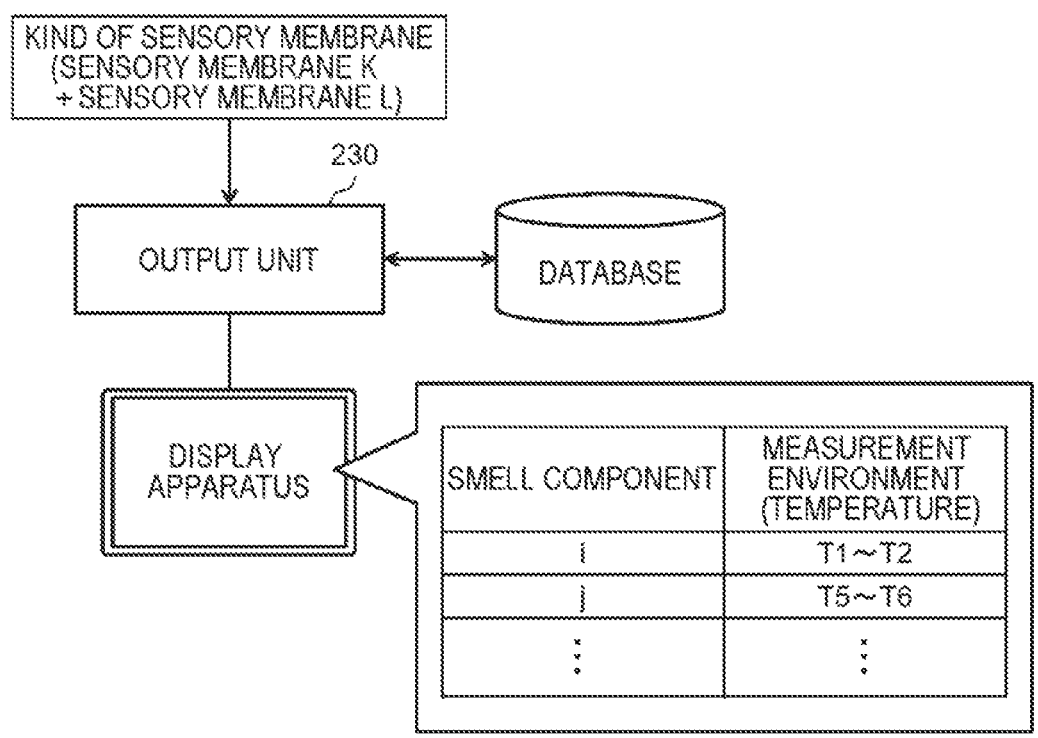
FIG. 10 is a diagram illustrating a flow in which an output unit outputs information to a display apparatus.

As one example, the output unit 230 can output information indicating a recommended measurement environment for each kind of smell component, with input of information indicating a configuration of a sensor 10 (a kind of sensory membrane being set in the sensor 10). As a specific example, it is assumed that the output unit 230 acquires input information indicating a combination of a sensory membrane K and a sensory membrane L in a state where information as illustrated in FIG. 9 is stored in the storage area. FIG. 9 is a diagram illustrating one example of a database constructed in the third example embodiment. In this case, the output unit 230 determines, based on the input information, information indicating a "smell component i" and a "temperature range of T1 to T2" and information indicating a "smell component j" and a "temperature range of T5 to T6", from the information illustrated in FIG. 9. Then, the output unit 230 outputs the determined information (information indicating a recommended measurement environment for each kind of smell component) to a display apparatus connected to the information processing apparatus 20 (example: FIG. 10). FIG. 10 is a diagram illustrating a flow in which the output unit 230 outputs information to the display apparatus.

In the present example, when a configuration of the sensor 10 is determined, information indicating a recommended measurement environment is output for each kind of smell component, by inputting information indicating the configuration of the sensor 10. With such information, a user of the sensor 10 can easily determine how to utilize the sensor 10 having the determined configuration (under what environment and for what smell component measurement is performed).

Figure 11:
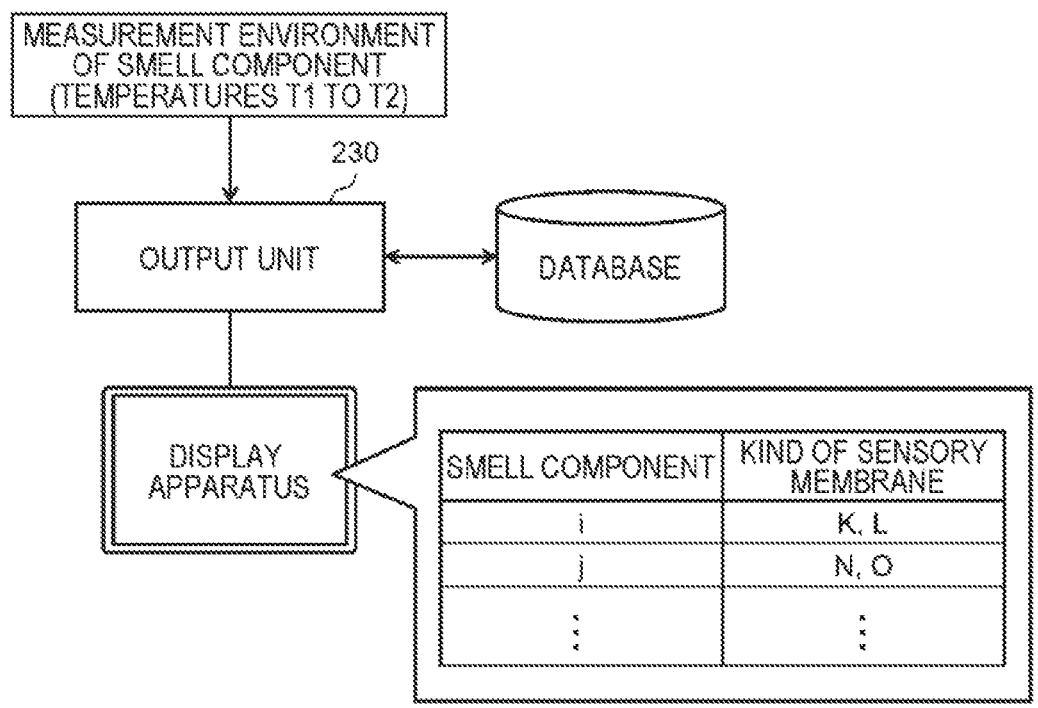
FIG. 11 is a diagram illustrating a flow in which the output unit outputs information to the display apparatus.

As another example, the output unit 230 can output information indicating a recommended configuration of the sensor 10 (a combination of sensory membranes) for each kind of smell component, with input of information indicating a measurement environment (an environment in which the sensor 10 is placed) of the smell component. As a specific example, it is assumed that the output unit 230 acquires input information indicating that temperature of a measurement environment is in a range of T1 to T2 in a state where information as illustrated in FIG. 9 is stored in the storage area. In this case, the output unit 230 determines, based on the input information, information indicating the "smell component i" and a "combination of the sensory membrane K and the sensory membrane L", and information indicating the "smell component j" and a "combination of a sensory membrane N and a sensory membrane O", from the information illustrated in FIG. 9. Then, the output unit 230 outputs the determined information (information indicating a recommended configuration of the sensor 10 for each kind of smell component) to a display apparatus connected to the information processing apparatus 20 (example: FIG. 11). FIG. 11 is a diagram illustrating a flow in which the output unit 230 outputs information to the display apparatus.

In the present example, when a measurement environment (an environment in which the sensor 10 is placed) is determined, information indicating a recommended configuration of the sensor 10 is output for each kind of smell component, by inputting information on the measurement environment. With such information, a user can be notified of what configuration of a sensor may be used for what smell in the determined measurement environment to enable stable measurement.

Figure 12:
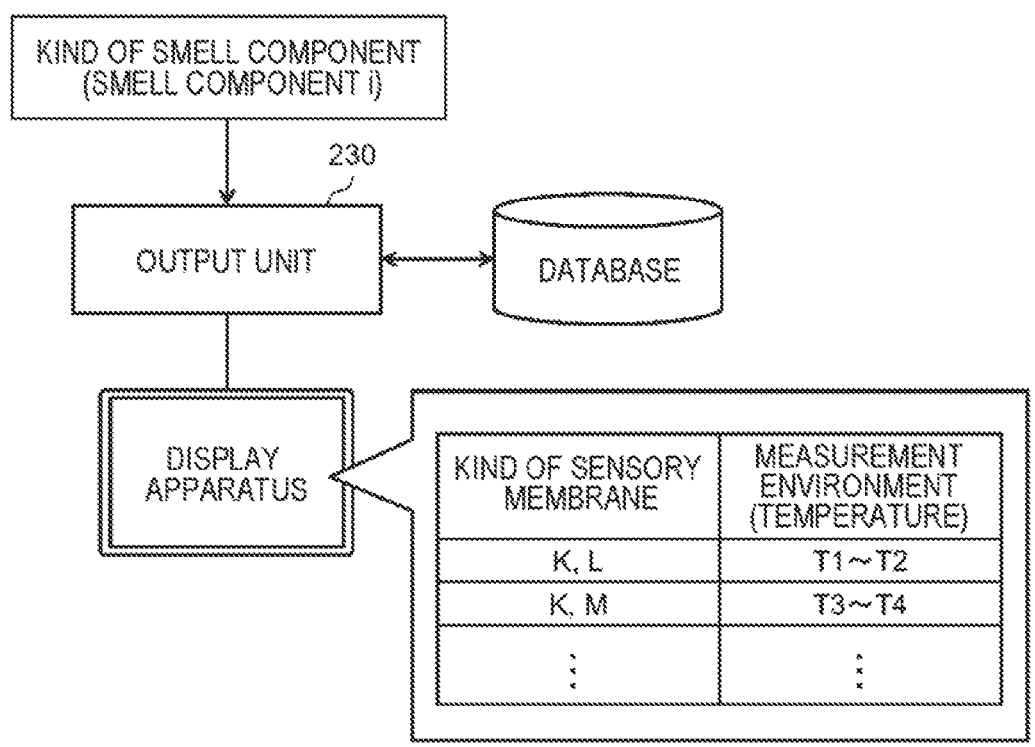
FIG. 12 is a diagram illustrating a flow in which the output unit outputs information to the display apparatus.

As another example, the output unit 230 can output information indicating a recommended configuration of the sensor 10 (a combination of sensory membranes) and a recommended measurement environment (a range of temperature or humidity, or the like), with input of information indicating a kind of smell component being a measurement target. As a specific example, it is assumed that the output unit 230 acquires input information indicating the "smell component i" as information on a smell component being a measurement target in a state where information as illustrated in FIG. 9 is stored in the storage area. In this case, the output unit 230 determines, based on the input information, information indicating a "combination of the sensory membrane K and the sensory membrane L" and a "temperature range of T1 to T2", and information indicating a "combination of the sensory membrane K and the sensory membrane M" and a "temperature range of T3 to T4", from the information illustrated in FIG. 9. Then, the output unit 230 outputs the determined information (information indicating a recommended configuration of the sensor 10 and a recommended measurement environment) to a display apparatus or the like connected to the information processing apparatus 20 (example: FIG. 12). FIG. 12 is a diagram illustrating a flow in which the output unit 230 outputs information to the display apparatus.

In the present example, when a smell component to be a measurement target is determined, information indicating a configuration of the sensor 10 and a measurement environment that are suited to measurement of the smell component is output, by inputting information on the smell component. With such information, a user becomes able to easily determine "what configuration of a smell sensor to prepare and under what environment the smell sensor is operated in order to accurately perform a discrimination analysis of a smell component being a target".

Figure 13:
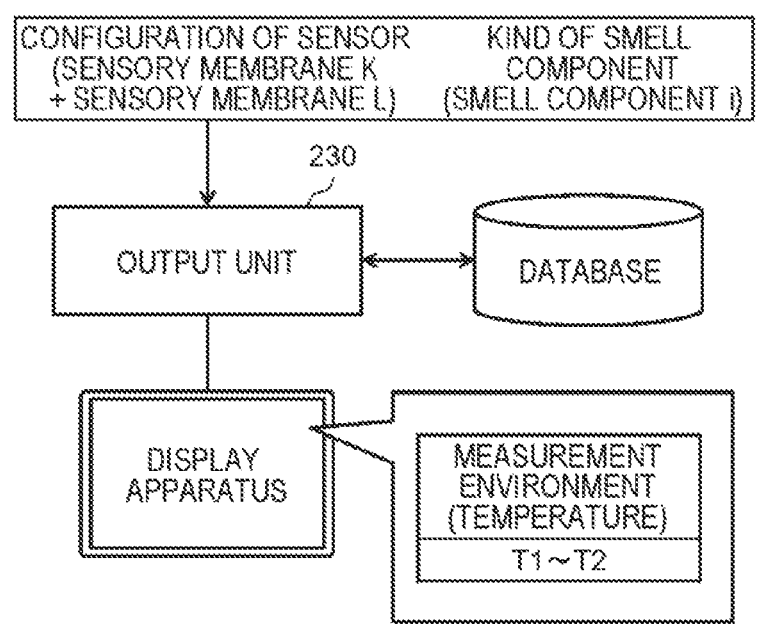
FIG. 13 is a diagram illustrating a flow in which the output unit outputs information to the display apparatus.

As another example, the output unit 230 can output information indicating a recommended measurement environment (a range of temperature or humidity, or the like), with input of information indicating a configuration of the sensor 10 (a combination of sensory membranes) and a kind of smell component being a measurement target. As a specific example, it is assumed that the output unit 230 acquires input information indicating a combination of the sensory membrane K and the sensory membrane L and the smell component i in a state where information as illustrated in FIG. 9 is stored in the storage area. In this case, the output unit 230 determines, based on the input information, information indicating a "temperature range of T1 to T2", from among pieces of the information illustrated in FIG. 9. Then, the output unit 230 outputs the determined information (information indicating a recommended measurement environment) to a display apparatus or the like connected to the information processing apparatus 20 (example: FIG. 13). FIG. 13 is a diagram illustrating a flow in which the output unit 230 outputs information to the display apparatus.

In the present example, when a configuration of a smell sensor and a smell component to be measured with the smell sensor are determined, information indicating a recommended measurement environment is output, by inputting information on the configuration of the smell sensor and the smell component. With such information, a user of the sensor 10 can easily recognize an environment in which measurement can be performed with stable accuracy.

Figure 14:
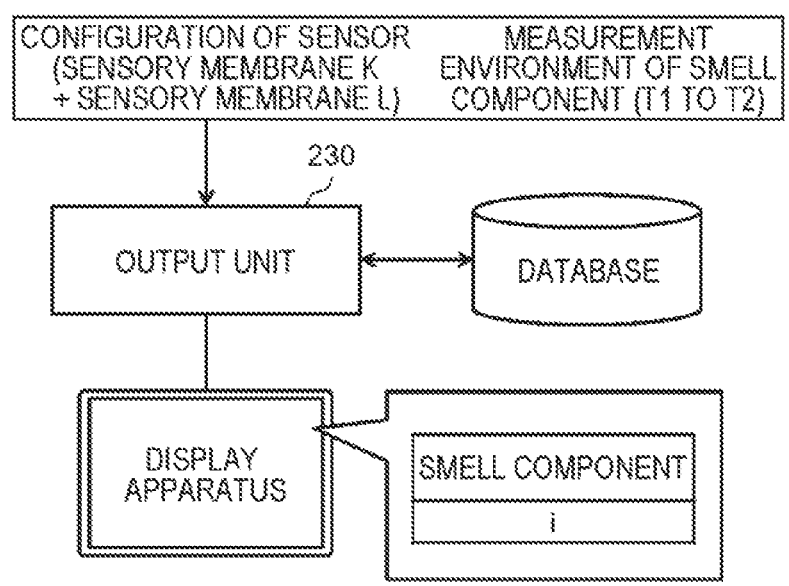
FIG. 14 is a diagram illustrating a flow in which the output unit outputs information to the display apparatus.

As another example, the output unit 230 can output information indicating a kind of smell component recommended as a measurement target, with input of information indicating a configuration of the sensor 10 (a combination of sensory membranes), and information indicating a measurement environment (an environment in which the sensor 10 is placed) of a smell component. As a specific example, it is assumed that the output unit 230 acquires input information indicating a combination of the sensory membrane K and the sensory membrane L and a temperature range of T1 to T2 in a state where information as illustrated in FIG. 9 is stored in the storage area. In this case, the output unit 230 determines, based on the input information, information indicating the "smell component i". Then, the output unit 230 outputs the determined information indicating a kind of smell component (the smell component i) to a display apparatus or the like connected to the information processing apparatus 20 (example: FIG. 14). FIG. 14 is a diagram illustrating a flow in which the output unit 230 outputs information to the display apparatus.

In the present example, when a configuration of a smell sensor and an environment in which the smell sensor is placed are already known, information indicating a smell component recommended as a measurement target is output, by inputting information on the configuration of the smell sensor and the environment. With such information, a user of the sensor 10 can easily recognize a smell component suited to measurement.

Figure 15:
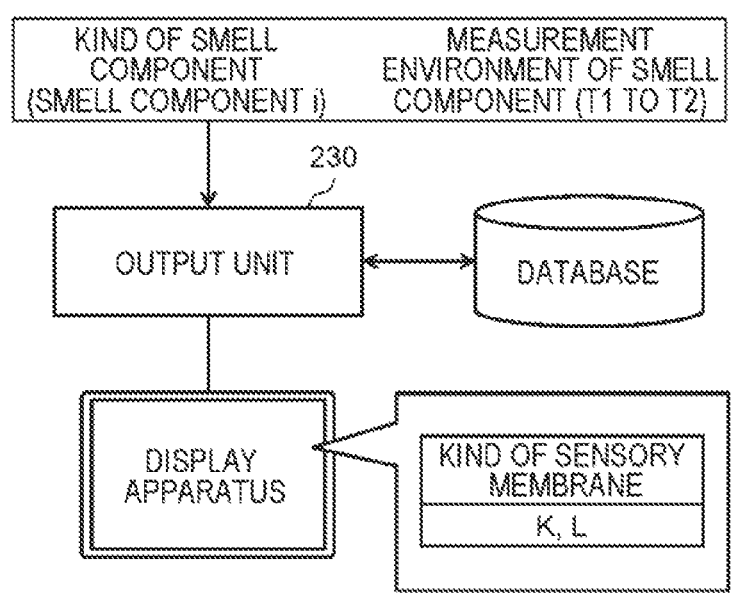
FIG. 15 is a diagram illustrating a flow in which the output unit outputs information to the display apparatus.

As another example, the output unit 230 can output information indicating a recommended configuration of the sensor 10 (a combination of sensory membranes), with input of information indicating a kind of smell component being a measurement target and a measurement environment (an environment in which the sensor 10 is placed) of the smell component. As a specific example, it is assumed that the output unit 230 acquires input information indicating the smell component i and a temperature range of T1 to T2 in a state where information as illustrated in FIG. 9 is stored in the storage area. In this case, the output unit 230 determines, based on the input information, information indicating a "combination of the sensory membrane K and the sensory membrane L", from among pieces of the information illustrated in FIG. 9. Then, the output unit 230 outputs the determined information (information indicating a recommended configuration of the sensor 10) to a display apparatus or the like connected to the information processing apparatus 20 (example: FIG. 15). FIG. 15 is a diagram illustrating a flow in which the output unit 230 outputs information to the display apparatus.

In the present example, when a smell component to be a measurement target and an environment in which the smell component is measured are already known, information indicating a recommended configuration of the sensor 10 (a combination of sensory membranes) is output, by inputting information on the smell component and the environment. With such information, even an inexperienced person can easily determine a sensory membrane to be set in the sensor 10.

Figure 16:
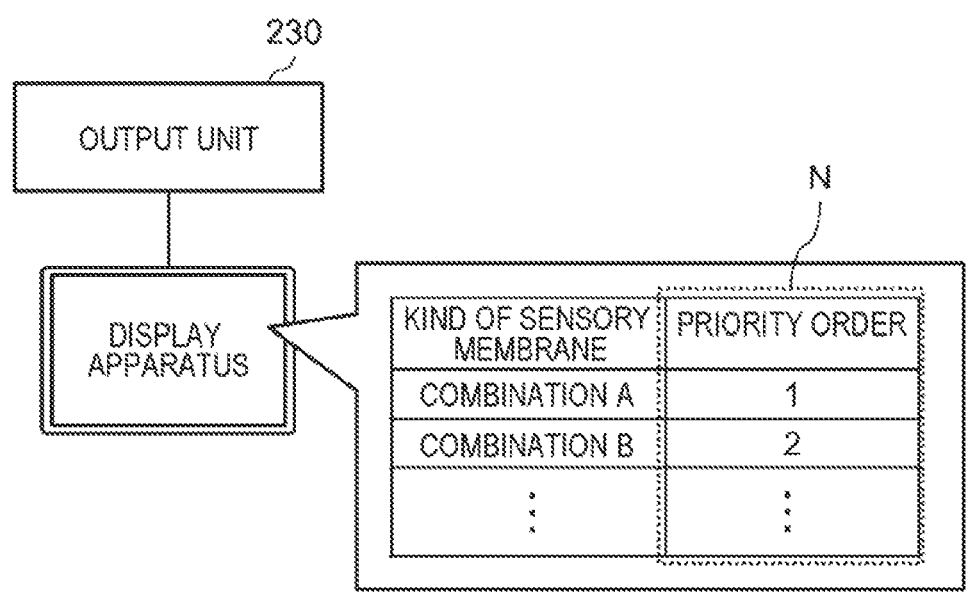
FIG. 16 is a diagram illustrating a flow in which the output unit outputs information to the display apparatus.

Moreover, when information indicating a plurality of smell components being measurement targets is acquired as an input together with information indicating a measurement environment, the output unit 230 can also determine a priority order of a configuration of the sensor 10, based on information on the database acquired in the third example embodiment. Specifically, it is assumed that, in a range of a measurement environment indicated by input information, there exist a combination A of sensory membranes in which a ratio of first-order lag transfer function feature values becomes constant (an inclination is 0) with regard to all the smell components indicated by the input information, and a combination B of sensory membranes in which a ratio of first-order lag transfer function feature values does not become constant (an inclination is not 0) with regard to at least some of the smell components. In this case, the output unit 230 gives a higher priority to the combination A that enables an analysis with stable accuracy with regard to all the smell components than the combination B. Then, the output unit 230 outputs information indicating a priority for each combination to a display apparatus or the like connected to the information processing apparatus 20 (example: FIG. 16). FIG. 16 is a diagram illustrating a flow in which the output unit 230 outputs information to the display apparatus. In the example of FIG. 16, the output unit 230 outputs a number N indicating a priority in association with each configuration of the sensor 10. With such information, a user can easily determine a configuration of the sensor 10 best suited to measurement.

Fourth Example Embodiment

In the present example embodiment, another example of application of a first-order lag transfer function feature value is described. When two or more sensory membranes of the same kind are set in a sensor 10, an information processing apparatus 20 can inspect performance of each of the sensory membranes by use of a first-order lag transfer function feature value for each sensory membrane.
<Functional Configuration>

Figure 17:
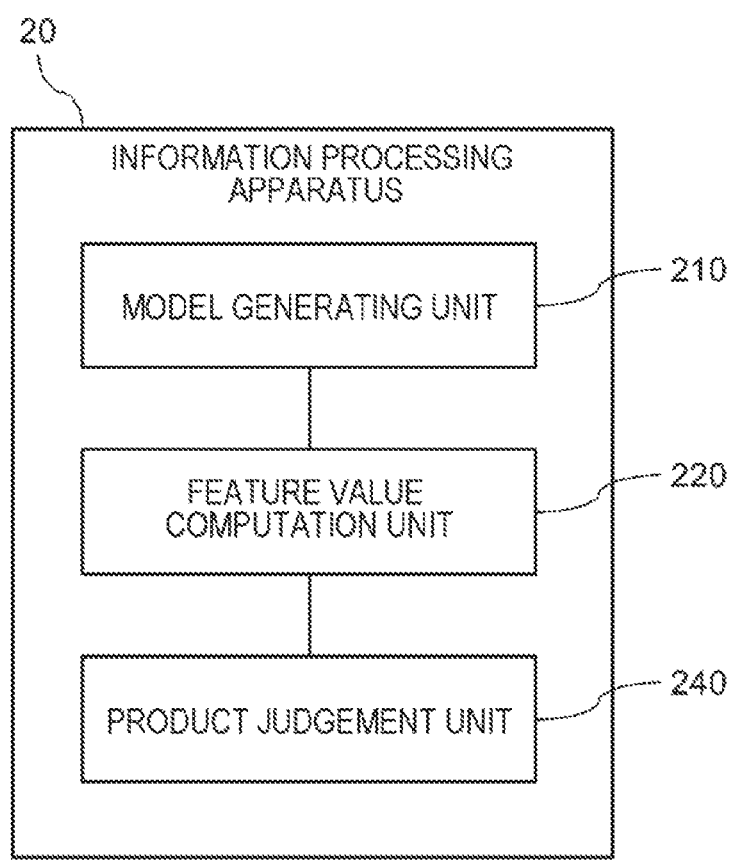
FIG. 17 is a diagram illustrating a functional configuration of an information processing apparatus according to a fourth example embodiment.

FIG. 17 is a diagram illustrating a functional configuration of the information processing apparatus 20 according to a fourth example embodiment. As illustrated in FIG. 17, the information processing apparatus 20 according to the present example embodiment further includes a product judgement unit 240. The product judgement unit 240 judges whether a first sensory membrane is an acceptable product, by use of a ratio between a first-order lag transfer function feature value of the sensory membrane (first sensory membrane) being an inspection target and a first-order lag transfer function feature value of a sensory membrane (second sensory membrane) to be a reference.
<Flow of Processing>

Figure 18:
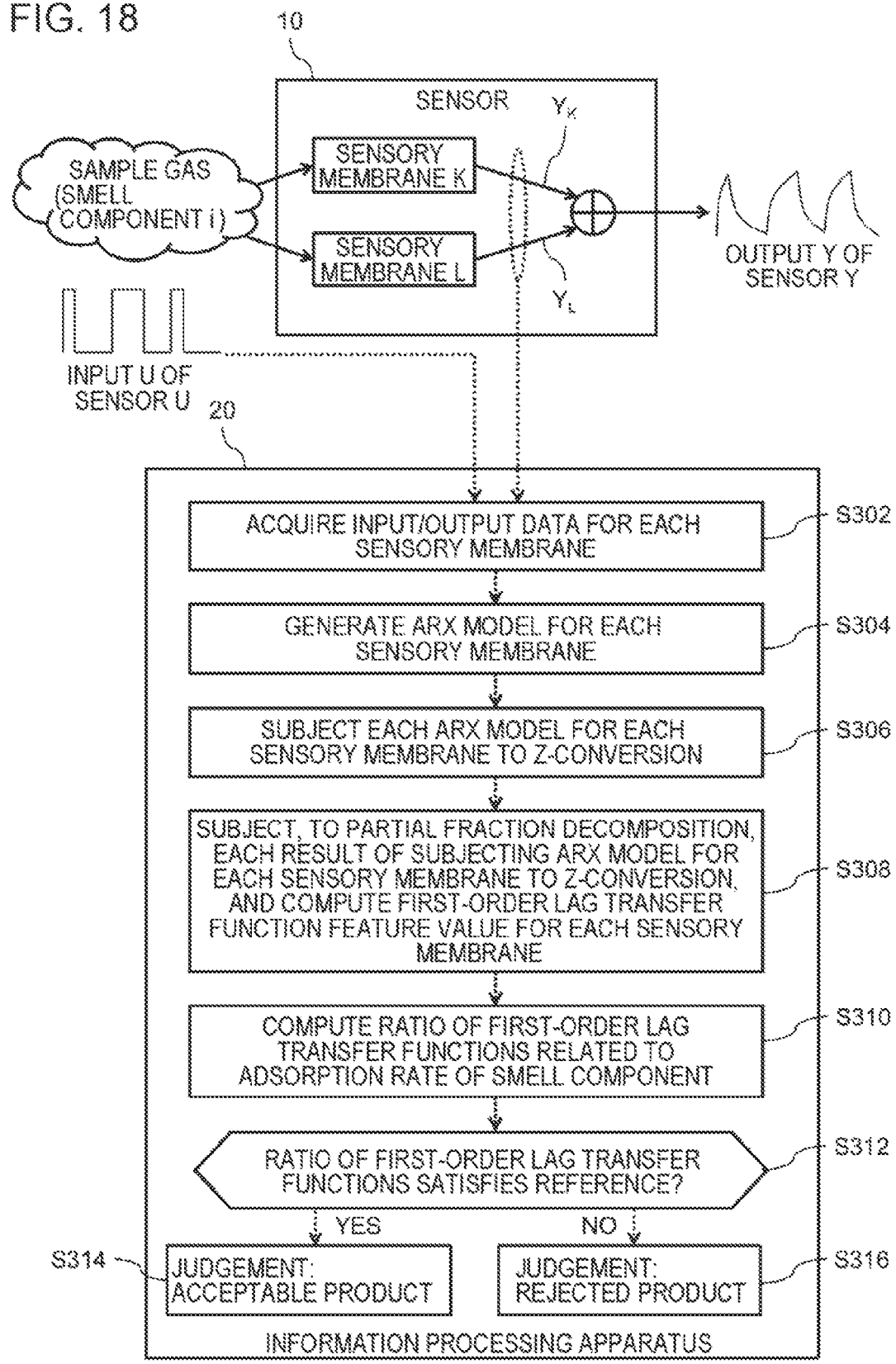
FIG. 18 is a diagram illustrating a flow of processing executed by the information processing apparatus according to the fourth example embodiment.

FIG. 18 is a diagram illustrating a flow of processing executed by the information processing apparatus 20 according to the fourth example embodiment. In the example of FIG. 18, the sensor 10 has two sensory membranes (a sensory membrane K and a sensory membrane L) of the same kind. The sensory membrane K is a sensory membrane being an inspection target, and the sensory membrane L is a sensory membrane having performance to be a reference. Moreover, in the example of FIG. 18, sample gas having a smell component i is input to the sensor 10 in response to an input signal U (e.g., an M-sequence signal) having a random sampling period. An output Y of the sensor 10 in this case is a sum of an output of the sensory membrane K and an output of the sensory membrane L.

First, a model generating unit 210 acquires input/output data for each sensory membrane, in response to measurement of the sample gas including a smell component i (S302). Then, the model generating unit 210 generates an ARX model for each sensory membrane, based on input/output data for each sensory membrane (S304). Then, the feature value computation unit 220 subjects the ARX model for each sensory membrane to Z-Transform (S306). Further, the feature value computation unit 220 computes a first-order lag transfer function feature value $(a_i, b_i)$ for each sensory membrane by subjecting, to partial fraction decomposition, a result of subjecting the ARX model to Z-Transform (S308). The processing in S302 to S308 is similar to the processing in S102 to S108 in FIG. 4.

Then, the feature value computation unit 220 computes a ratio $(b_{iK}/b_{iL})$ of the first-order lag transfer function feature values $b_i$s related to an adsorption rate of the smell component i, with regard to the sensory membrane K and the sensory membrane L (S310). Herein, when the sensory membrane K and the sensory membrane L have the same performance, a first-order lag transfer function feature value of each of the sensory membranes becomes equal. In this case, a value of $b_{iK}/b_{iL}$ becomes 1. Thus, the product judgement unit 240 judges whether $b_{iK}/b_{iL}$ satisfies a predetermined reference ($b_{iK}/b_{iL}$ becomes 1 or a value close to 1) (S312). When $b_{iK}/b_{iL}$ satisfies the predetermined reference (S312: YES), the product judgement unit 240 judges that the sensory membrane K being an inspection target is an "acceptable product having performance equal to the sensory membrane L being a reference product" (S314). On the other hand, when $b_{iK}/b_{iL}$ does not satisfy the predetermined reference (S312: NO), the product judgement unit 240 judges that the sensory membrane K being an inspection target is a "rejected product that does not have performance equal to the sensory membrane L being a reference product" (S316).

In consequence, the present example embodiment enables to determine whether performance of a sensory membrane is good/poor, by using a first-order lag transfer function feature value acquired by the method described in the first example embodiment.

Fifth Example Embodiment

In the present example embodiment, another example of application of a first-order lag transfer function feature value is described. When two or more sensory membranes of the same kind are set in a sensor 10, an information processing apparatus 20 can correct an individual difference (a margin of error of output performance) between the sensory membranes by use of a first-order lag transfer function feature value for each sensory membrane.
<Functional Configuration>

Figure 19:
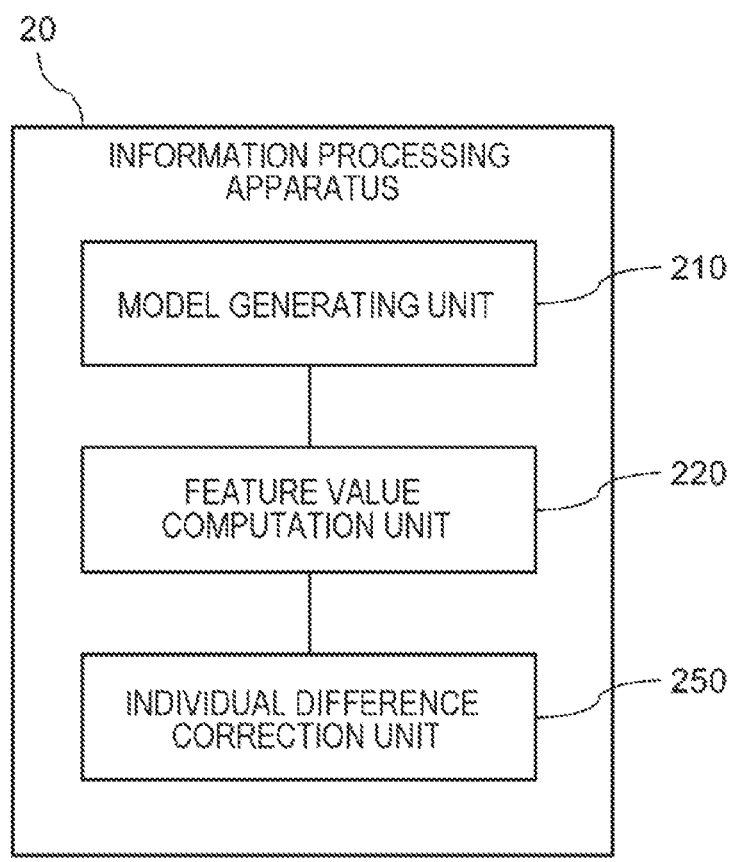
FIG. 19 is a diagram illustrating a functional configuration of an information processing apparatus according to a fifth example embodiment.

FIG. 19 is a diagram illustrating a functional configuration of the information processing apparatus 20 according to a fifth example embodiment. As illustrated in FIG. 19, the information processing apparatus 20 according to the present example embodiment further includes an individual difference correction unit 250. The individual difference correction unit 250 corrects an individual difference between two sensory membranes of the same kind, by use of a ratio of first-order lag transfer function feature values of the two sensory membranes.

<Flow of Processing>

Figure 20:
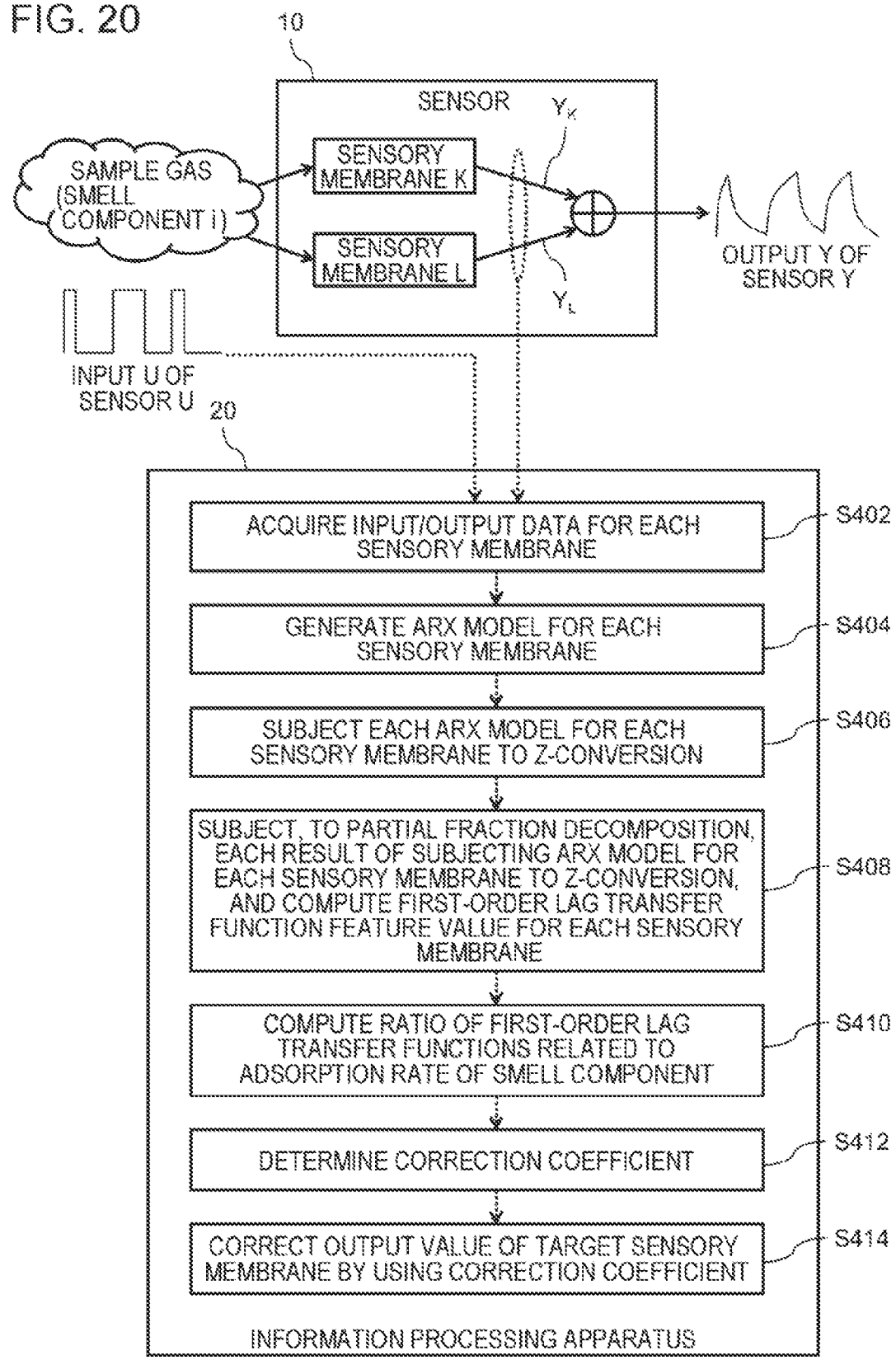
FIG. 20 is a diagram illustrating a flow of processing executed by the information processing apparatus according to the fifth example embodiment.

FIG. 20 is a diagram illustrating a flow of processing executed by the information processing apparatus 20 according to the fifth example embodiment. In the example of FIG. 20, the sensor 10 has two sensory membranes (a sensory membrane K and a sensory membrane L) of the same kind. Moreover, in the example of FIG. 20, sample gas having a smell component i is input to the sensor 10 in response to an input signal U (e.g., an M-sequence signal) having a random sampling period. An output Y of the sensor 10 in this case is a sum of an output of the sensory membrane K and an output of the sensory membrane L.

First, a model generating unit 210 acquires input/output data for each sensory membrane, in response to measurement of the sample gas including a smell component i (S402). Then, the model generating unit 210 generates an ARX model for each sensory membrane, based on input/output data for each sensory membrane (S404). Then, the feature value computation unit 220 subjects the ARX model for each sensory membrane to Z-Transform (S406). Further, the feature value computation unit 220 computes a first-order lag transfer function feature value ($a_i$, $b_i$) for each sensory membrane by subjecting, to partial fraction decomposition, a result of subjecting the ARX model to Z-Transform (S408). The processing in S402 to S408 is similar to the processing in S102 to S108 in FIG. 4.

Then, the feature value computation unit 220 computes a ratio ($b_{iK}/b_{iL}$) of the first-order lag transfer function feature values $b_i$s related to an adsorption rate of the smell component i, with regard to the sensory membrane K and the sensory membrane L (S410). The individual difference correction unit 250 determines a correction coefficient for correcting an output value of either one of the sensory membrane K and the sensory membrane L, based on the ratio ($b_{iK}/b_{iL}$) between a first-order lag transfer function feature value $b_{iK}$ and a first-order lag transfer function feature value $b_{iL}$ acquired by the processing in S410 (S412). Specifically, the individual difference correction unit 250 determines a reciprocal number of $b_{iK}/b_{iL}$ as a correction coefficient for the output value of the sensory membrane K, and stores the determined correction coefficient in a memory 1060 or the like. Alternatively, the individual difference correction unit 250 may determine $b_{iK}/b_{iL}$ as a correction coefficient for the output value of the sensory membrane L, and stores the determined correction coefficient in the memory 1060 or the like. Then, the individual difference correction unit 250 corrects the output value of the sensory membrane K or the sensory membrane L by use of the correction coefficient determined in S412 (S414).

In the present example embodiment, an individual difference for each sensory membrane is corrected by way of software. Variation in accuracy of an analysis of the sensor 10 can be prevented by equalizing performance of each sensory membrane.

While the example embodiments of the present invention have been described above with reference to the drawings, the present invention should not be limited to the example embodiments and interpreted accordingly, and various modifications, improvements, and the like can be made based on knowledge of a person skilled in the art without departing from the spirit of the present invention. Various inventions can be formed by a suitable combination of a plurality of components disclosed in the example embodiments. For example, some of all the components indicated in the example embodiments may be deleted, or components in differing example embodiments may be suitably combined. Moreover, in each example embodiment, an order of illustrated processes (steps) can be altered to the extent consistent with contents.

The invention claimed is:

1. An information processing apparatus comprising:
   a model generating unit that generates an Auto-Regressive with eXogenous input (ARX) model of a smell sensor by use of input data controlling an input operation of gas including a smell component being a measurement target, and output data being acquired by inputting the gas to the smell sensor, based on the input data; and
   a feature value computation unit that computes a transfer function of the smell sensor relating to the smell component by subjecting the ARX model to Z-Transform, and further computes a first-order lag transfer function feature value of the smell sensor relating to the smell component by subjecting the transfer function to partial fraction decomposition.

2. The information processing apparatus according to claim 1, wherein
   the model generating unit
      extracts a plurality of pieces of partial input data and a plurality of pieces of partial output data from the input data and the output data by use of a plurality of windows, and
      generates a plurality of ARX models by use of the plurality of pieces of partial input data and the plurality of pieces of partial output data, and
   the feature value computation unit
      computes a plurality of the first-order lag transfer function feature values by use of the plurality of ARX models.

3. The information processing apparatus according to claim 1, wherein
   the smell sensor comprises a first sensory membrane and a second sensory membrane,
   the model generating unit
      acquires the input data when the gas is measured in a plurality of measurement environments, and the output data for each of the sensory membranes, and
      generates a plurality of ARX models for each of the sensory membranes by use of the input data and the output data for each of the sensory membranes, and
   the feature value computation unit
      computes a plurality of the first-order lag transfer function feature values for each of the sensory membranes by use of the ARX model for each of the sensory membranes generated with regard to each of the plurality of measurement environments,
      determines a measurement environment in which a ratio of the plurality of first-order lag transfer function feature values each computed for each of the sensory membranes satisfies a reference, and
      stores information indicating the determined measurement environment in a storage area.

4. The information processing apparatus according to claim 1, wherein
   the smell sensor comprises a first sensory membrane being an inspection target and a second sensory membrane being a reference, the model generating unit generates an ARX model for each of the sensory membranes by use of the input data and the output data for each of the sensory membranes, the feature value computation unit
computes the first-order lag transfer function feature value for each of the sensory membranes by use of the ARX model for each of the sensory membranes, the information processing apparatus further comprising a judgement unit that judges whether the first sensory membrane is an acceptable product, by whether a ratio of the first-order lag transfer function feature values each computed for each of the sensory membranes satisfies a reference.

5. An information processing method executed by a computer, the method comprising:

generating an Auto-Regressive with eXogenous input (ARX) model of a smell sensor by use of input data controlling an input operation of gas including a smell component being a measurement target, and output data being acquired by inputting the gas to the smell sensor, based on the input data; and computing a transfer function of the smell sensor relating to the smell component by subjecting the ARX model to Z-Transform, and further computing a first-order lag transfer function feature value of the smell sensor relating to the smell component by subjecting the transfer function to partial fraction decomposition.

6. The information processing method executed by a computer according to claim 5, the method further comprising:

extracting a plurality of pieces of partial input data and a plurality of pieces of partial output data from the input data and the output data by use of a plurality of windows;

generating a plurality of ARX models by use of the plurality of pieces of partial input data and the plurality of pieces of partial output data; and computing a plurality of the first-order lag transfer function feature values by use of the plurality of ARX models.

7. The information processing method according to claim 5, wherein the smell sensor comprises a first sensory membrane and a second sensory membrane, the information processing method further comprising by the computer, acquiring the input data when the gas is measured in a plurality of measurement environments, and the output data for each of the sensory membranes, generating a plurality of ARX models for each of the sensory membranes by use of the input data and the output data for each of the sensory membranes, computing a plurality of the first-order lag transfer function feature values for each of the sensory membranes by use of the ARX model for each of the sensory membranes generated with regard to each of the plurality of measurement environments, determining a measurement environment in which a ratio of the plurality of first-order lag transfer function feature values each computed for each of the sensory membranes satisfies a reference, and storing information indicating the determined measurement environment in a storage area.

8. The information processing method according to claim 5, wherein the smell sensor comprises a first sensory membrane being an inspection target and a second sensory membrane being a reference, the information processing method further comprising by the computer, generating an ARX model for each of the sensory membranes by use of the input data and the output data for each of the sensory membranes, computing the first-order lag transfer function feature value for each of the sensory membranes by use of the ARX model for each of the sensory membranes, and judging whether the first sensory membrane is an acceptable product, by whether a ratio of the first-order lag transfer function feature values each computed for each of the sensory membranes satisfies a reference.

9. A non-transitory computer readable medium storing a program causing a computer to execute an information processing method, the method comprising:

generating an Auto-Regressive with eXogenous input (ARX) model of a smell sensor by use of input data controlling an input operation of gas including a smell component being a measurement target, and output data being acquired by inputting the gas to the smell sensor, based on the input data; and computing a transfer function of the smell sensor relating to the smell component by subjecting the ARX model to Z-Transform, and further computing a first-order lag transfer function feature value of the smell sensor relating to the smell component by subjecting the transfer function to partial fraction decomposition.

* * * * *